United States Patent [19]
Hochstein

[11] Patent Number: 5,413,587
[45] Date of Patent: May 9, 1995

[54] INFRARED HEATING APPARATUS AND METHODS

[76] Inventor: Peter A. Hochstein, 2966 River Valley Dr., Troy, Mich. 48098

[21] Appl. No.: 155,924

[22] Filed: Nov. 22, 1993

[51] Int. Cl.$^6$ .................................. A61N 5/06
[52] U.S. Cl. .................................. 607/100
[58] Field of Search .................. 607/88–96, 607/100; 219/553, 530–532, 10.55 D, 10.55 R, 10.57

[56] References Cited

U.S. PATENT DOCUMENTS

| | | | |
|---|---|---|---|
| 2,545,805 | 3/1951 | Callender | 219/531 |
| 2,634,361 | 4/1953 | Reynolds | 219/531 |
| 3,867,948 | 2/1975 | Kallenborn | 607/88 |
| 4,140,130 | 2/1979 | Storm, III . | |
| 4,207,456 | 6/1980 | Best | 219/345 |
| 4,461,299 | 7/1984 | Guibert | 607/96 |
| 4,489,234 | 12/1984 | Harnden, Jr. et al. | 219/347 |
| 4,501,275 | 2/1985 | Maahs . | |
| 4,717,813 | 1/1988 | Berg et al. | 219/553 X |
| 4,931,626 | 6/1990 | Shikama et al. | 219/530 X |
| 5,028,760 | 7/1991 | Okuyama | 219/530 X |
| 5,128,514 | 7/1992 | Lehmann et al. | 219/553 X |
| 5,186,181 | 2/1993 | Franconi et al. . | |

FOREIGN PATENT DOCUMENTS

| | | | |
|---|---|---|---|
| 0134323 | 3/1985 | European Pat. Off. | 607/103 |
| 2350552 | 4/1977 | France . | |
| 2831013 | 1/1980 | Germany | 607/93 |
| 4113803 | 10/1992 | Germany | 607/100 |
| 7204427 | 10/1973 | Netherlands . | |
| 8100677 | 3/1981 | WIPO . | |
| 9007358 | 7/1990 | WIPO . | |

OTHER PUBLICATIONS

Meyer J. L., Kapp D. S., Normal-tissue Effects of Hyperthermia. Front. Radiat. Ther. Oncol. 1989; 23:162–76.

Hetzel F. W., Biologic Rationale for Hyperthermia, Radiol. Clin. North Am. 1989 May;27(3):499–508.

Robins H. I., Dennis W. H., Neville A. J., Shecterle L. M., Martin P. A., Grossman J., Davis T. E., Neville S. R., Gillis W. K., and Rusy B. F., A Nontoxic System for 41.8 °C Whole-Body Hyperthermia: Results of a Phase I Study Using a Radiant Heat Device, Cancer Research 1985; 45:3937–3944.

Dunlop P. R., Howard G. C., Has Hyperthermia a Place in Cancer Treatment?, Clin. Radiol. 1989 Jan.; 40(1):76–82.

Westerhof W., Siddiqui A. H., Cormane R. H., and Scholten A., Infrared Hyperthermia and Psoriasis, Arch. Dermatol. Res. 1987; 279(3):209–10.

Gogia P. P., Hurt B. S., and Zirn T. T., Wound Management with Whirlpool and Infrared Cold Laser Treatment, Phys. Ther. 1988 Aug.; 68(8):1239–42.

Koltyn K. F., Robins H. I., Schmitt C. L., Cohen J. D., and Morgan W. P., Changes in Mood State Following Whole-body Hyperthermia, Int. J. Hyperthermia, 1992; 8(3):305–307.

*Primary Examiner*—Angela D. Sykes
*Attorney, Agent, or Firm*—Reising, Ethington, Barnard, Perry & Milton

[57] ABSTRACT

An apparatus (10,80,150) for heating an object with black body infrared radiation. The apparatus (10,80,150) comprises a radiation source (42,96,158) for generating black body infrared radiation and a honeycomb stagnating element (48,132,160) for preventing transmission of heat by convection from the radiation source (42,96,158). Also various methods for using the apparatus (10,80,150) are disclosed.

16 Claims, 4 Drawing Sheets

INFRARED HEATING APPARATUS AND METHODS

TECHNICAL FIELD

The subject invention relates to an apparatus for generating infrared radiation, and more particularly to an apparatus and method used for irradiating an object with black body infrared radiation.

BACKGROUND ART

The therapeutic benefits attributable to hyperthermia, i.e. elevated body temperature, as a treatment for many types of bodily disorders have been known for centuries. The common fever elegantly exemplifies the therapeutic benefits of elevated body temperature. In the presence of infection by common infectious agents, e.g., cold viruses, the human immune system responds by elevating the body's core temperature to aid in the resolution of the infection.

Throughout history, practitioners have sought to induce fever or an artificial state of fever in order to increase body temperature to treat bodily disorders. An early form of treatment for syphilis illustrates this fact. Historically, practitioners attempted to artificially elevate the body temperature of an individual infected with syphilis by such medieval methods as infecting the patient with an infectious agent, such as malaria, thereby to induce a fever in an attempt to cure the syphilis. This method, however, even if successful in curing the syphilis, left the patient chronically infected with the incurable disease of malaria.

Modern approaches toward achieving localized hyperthermia in biological tissues include dielectric heating, microwave diathermy, ultrasonic heating, and the application of hot compresses or "hot packs". All of these methods have particular clinical applications, but each exhibits one or more disadvantages.

Dielectric heating involves placing capacitative electrodes around the tissue to be treated. An alternating R.F. (radio frequency) current of between $10^6$ Hz to $10^9$ Hz is applied across the tissues and induces a dielectric loss within the tissues. This dielectric loss within the tissues results in heat generated within the tissues themselves. The excellent tissue penetration afforded by this heating modality make it an obvious choice for the deep heating of tissues. However, the need for accuracy in the placement of the electrodes and the attendant loss of control of the field location within the tissues associated with electrode placement, make heating a specific region of tissue difficult.

Microwave diathermy is an extension of the dielectric heating method. Microwave diathermy employing R.F. frequencies in the range of $10^9$ Hz to $10^{10}$ Hz were found to be very efficacious, but the result were plagued by various troubling effects which often outweighed the benefits. Human tissues exhibit a highly variable impedance or radiation resistance to the particular wavelengths of electromagnetic radiation employed in microwave diathermy. This variability in impedance may cause constructive interference, destructive interference, or even resonance within the tissues resulting in damaging localized heating or pain. Additionally, if the subject undergoing microwave diathermy treatment has any metallic implants such as hip joint replacements plates or pins, these implants would further concentrate the radiation and cause damage to local tissues. Microwave diathermy was commonly used until concerns over the effects of high electromagnetic (e.m.) field intensities on biologic subjects dampened the enthusiasm for this modality.

Ultrasonic diathermy is a commonly employed heating modality used in physical therapy settings to locally heat sub-surface or deep tissues to provide pain relief. These ultrasonic devices emit energy at frequencies from between $2 \times 10^4$ to $10^7$. Heating of the tissues occurs because of visco-elastic loss within the tissues in response to mechano-elastic waves coupled into the tissues from an ultrasonic transducer. The variability of the impedance of human tissues can give rise to reflections at tissue interfaces such as at the muscle-bone interface or muscle-fat interface. These reflections can result in localized concentrations of energy referred to as "hot spotting" which can lead to tissue damage or subject the patient to unnecessary pain. In addition, in order to implement this modality of heating tissue, the transducer must be continuously moved over the treatment area and a messy coupling gel must be applied to the patient in order for the patient to receive the ultrasonic waves.

Both the radio frequency diathermy devices and ultrasonic diathermy devices are relatively complex and costly to manufacture and do not lend themselves to unsupervised or non-medical applications of treatment.

People use heating pads and "hot packs" for treating a variety of aches, pains, and ailments. The benefits of these devices are limited; however, since the heat is deposited on the surface of the skin and must penetrate to the underlying tissues by conduction, effective treatment is limited skin tolerance to elevated temperatures.

Infrared radiation provides another modality for inducing localized hyperthermia in biological tissues. The epidermal tissue of the skin absorbs much of the infrared radiation of wavelengths shorter than 3 $\mu$m. In order to increase the internal temperature of biological tissues and, thereby, to induce localized hyperthermia without causing substantial heating of the epidermal tissue, application of infrared radiation of wavelengths in the range of 3–30 $\mu$m to the biological tissues are desired. Infrared radiation in the range of 3–30 $\mu$m is only partly absorbed by water molecules. Since epidermal tissue contains a greater proportion of water molecules than does deeper tissues such as fat, the infrared radiation in this range is not substantially absorbed by the epidermal tissue of the skin. A typical example of an infrared radiation source used for localized heating of biological tissues is a common heat lamp. The common heat lamp provides an inexpensive mechanism for generating infrared radiation. However, as is the case with all other prior art infrared radiation sources used for inducing localized hyperthermia, the prior art infrared sources generate a broad spectrum of infrared radiation including short wavelength infrared radiation of wavelengths less than 3 $\mu$m which overheat the epidermal tissues, i.e., the skin.

U.S. Pat. No. 4,489,234 to Harnden, Jr. et al. teaches a particular infrared wavelength heating and/or cooking device utilizing honeycomb tube members for supporting glass cover plates. However, the device produces infrared radiation of wavelengths substantially less than 3 $\mu$m. The wavelengths generated are best suited to heating and/or cooking but would cause serious damage if applied to biological tissues. Unfortunately, both the epidermal tissues, i.e. the skin, and the underlying tissues absorb infrared radiation of wavelengths shorter than 3 μm. As a result, the prior art infrared radiation generating devices detrimentally heat the epidermal tissues of the skin and cause the temperature of the skin to increase to levels causing discomfort or epidermal tissue damage. Because the epidermal tissue of the skin absorbs infrared radiation of wavelengths less than 3 μm as well as do the internal tissues, the prior art infrared hyperthermia devices limit administration of infrared radiation to less than the efficacious amounts necessary for achieving therapeutic benefit.

Medium and long wavelength infrared emitters are commonly used in industry to cure coatings and heat products. These infrared emitters typically utilize a heated, highly emissive surface to couple radiation through the air to object being heated. However, convective coupling of the air surrounding the emitter heats the air which can heat nearby objects by convection and conduction.

Lasers are an ideal source of monochromatic long wavelength infrared radiation. In particular, $CO_2$ lasers are a good source of monochromatic long wave infrared radiation. However, lasers of this type produce a very intense and discrete beam of focused infrared radiation which could cause tissue damage. These intense and discrete beams of infrared radiation could be diffused by expanding or scanning the beam, but this reduces the power intensity ($W/m^2$) making the laser a less effective modality of treatment. Lasers emit essentially at one wavelength. The disadvantage of emitting only a single wavelength, as opposed to a broad spectrum emitting source, is that the wavelength may be absorbed by a particular molecule or tissue. A broad spectrum emitting source increases the probability that the desired wavelengths will reach the tissues to be treated. Additionally, at this time, the high cost of the equipment, the complexity of the apparatus, i.e., sealed sources and infrared optics, and the need for trained operators preclude lasers from being a practical modality for generating long wavelength infrared radiation for inducing localized hyperthermia.

Efficiency of the radiation source is another significant problem associated with prior art radiant infrared wavelength generating devices. Typically, radiant infrared generating sources must be maintained in a temperature range of 300°–3000° K. to maximize radiative emission of infrared radiation. In particular, a radiation source designed to operate in the temperature range of 300°–3000° K. will lose efficiency due to convective heat loss to the surrounding air. This loss of efficiency due to convective and conductive heat loss requires a large input of electrical power to constantly maintain the temperature of the radiation generating source. Prior art devices have attempted to remedy this problem by operating the radiation source in a vacuum, i.e., an air-free environment. Typically, the radiation source is operated within a sealed and air-free or vacuum environment enclosed behind an infrared transparent window. While vacuum sealing is an effective mechanism for increasing the efficiency of a radiant infrared wavelength generating source for producing infrared radiation of <3 μm, however, longer wavelength infrared radiation in the range of 3–30 μm is absorbed by most practical window materials. Therefore, using this means for generating infrared radiation having wavelength substantially in the range of 3–30 μm for heating internal biological tissues with minimal heating of the external tissues is not practicable. While using a vacuum is effective at reducing convective and conductive heat losses from the radiation generating source, its use is impractical because most practical materials will not allow for the transmission of infrared wavelengths in the range of 3–30 μm. Window materials suitable for transmission of medium and long wavelength infrared radiation are available such as silicon, germanium, zinc selenide and other exotic materials. These materials, however, are physically unable to withstand the pressures associated with maintaining a vacuum in a sealed, evacuated radiation source.

In order to maximize the efficiency of a radiant radiation generating source capable of emitting infrared radiation of wavelengths in the range of 3–30 μm, it is necessary to find an alternative means for increasing efficiency of the radiation source capable of both preventing convective heat losses from the radiation generating source by inhibiting air flow at the radiation source and, at the same time, allows infrared radiation of wavelengths in the range of 3–30 μm to pass through it.

SUMMARY OF THE INVENTION

According to the present invention, an apparatus is provided for heating an object with black body infrared radiation. The apparatus comprises a radiation source for generating black body infrared radiation and emitting the radiation for transmission into a first zone and thereafter into a second zone to heat a body located in the second zone by black body infrared radiation. The apparatus is characterized by stagnating means disposed in the first and second zones to establish a continuous and homogenous fluid medium extending from the radiation source into the first zone and into the second zone. The stagnating means stagnates the flow of the fluid medium in the first zone to limit transmission of heat by convection from the radiation source and from the first zone to the second zone.

The resulting apparatus provides an effective mechanism for increasing the temperature of internal biological tissue without causing discomfort or damage to the overlying external biological tissues.

The present invention also includes a method of utilizing the novel apparatus for heating a body with black body infrared radiation.

The present invention also includes a method for heating internal biological tissues of the type also having external tissues without increasing the temperature of the external tissues above a predetermined limit where discomfort or damage to the external tissues occurs.

The present invention additionally includes a method for increasing localized blood circulation in internal biological tissues of the type also having external tissues without increasing the temperature of the external tissues above a predetermined limit where discomfort or damage to the external tissues occurs.

The present invention additionally includes a method for increasing localized blood circulation in internal biological tissues of a penis having external tissues without increasing the temperature of the external tissues above a predetermined limit where discomfort or damage to the external tissues occurs.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENTS

Figures 1, 2:
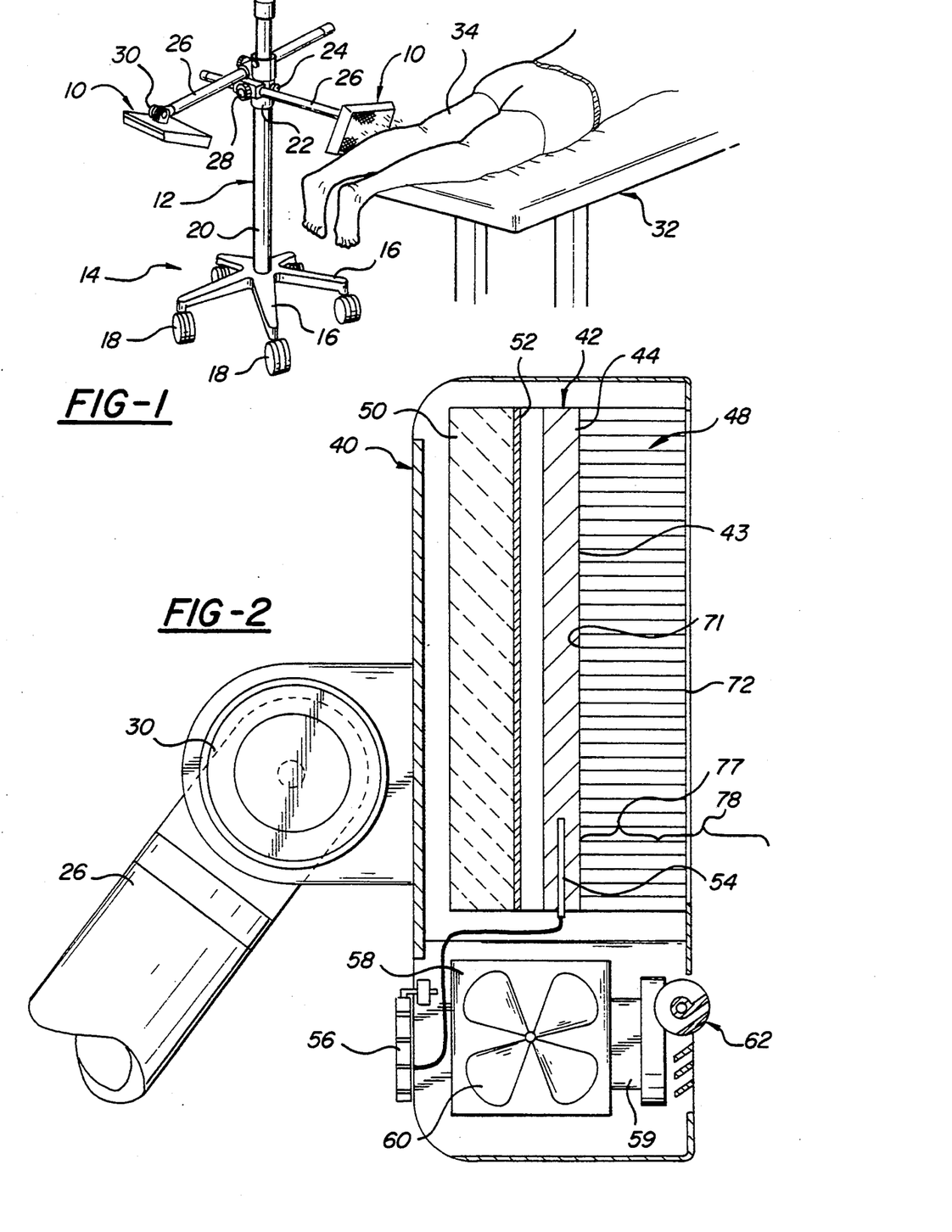
FIG. 1 is a perspective view of the heating apparatus of the present invention mounted on an adjustable stand, and showing a subject to be treated.
FIG. 2 is a side cross-sectional view of the heating apparatus of the invention.

Referring to FIG. 1, an infrared heating apparatus 10 according to the invention is shown mounted on a supporting stand 12 having a base 14 comprised of a plurality of legs 16 mounted on casters 18. A vertical post 20 is affixed to the base 14 having a clamping sleeve 22 slidably mounted thereon and a clamp 24 fixing the clamping sleeve at the desired height on the vertical post 20. A lateral arm 26 is also slidably mounted in the clamping sleeve 22 and affixed in the desired position by means of a clamp 28. Adjustable coupling means 30 is also provided at the end of each lateral arm 26 and is in turn affixed to the infrared heating apparatus 10. A table 32 is also shown supporting a subject 34 to be treated.

Referring to FIG. 2, the heating apparatus 10 of the invention is shown in greater detail, and comprises a housing 40 which may be formed of a temperature resistant material such as aluminum, or any other suitable material. Inside the housing 40 is a radiation source. The radiation source is a radiation generating element 42 comprised of a base block 44 formed of a material such as ceramic fibers or any other suitable material, and having a sinuated heating element 46 dispersed therethrough, as shown in greater detail in FIG. 3.

Figures 3, 4:
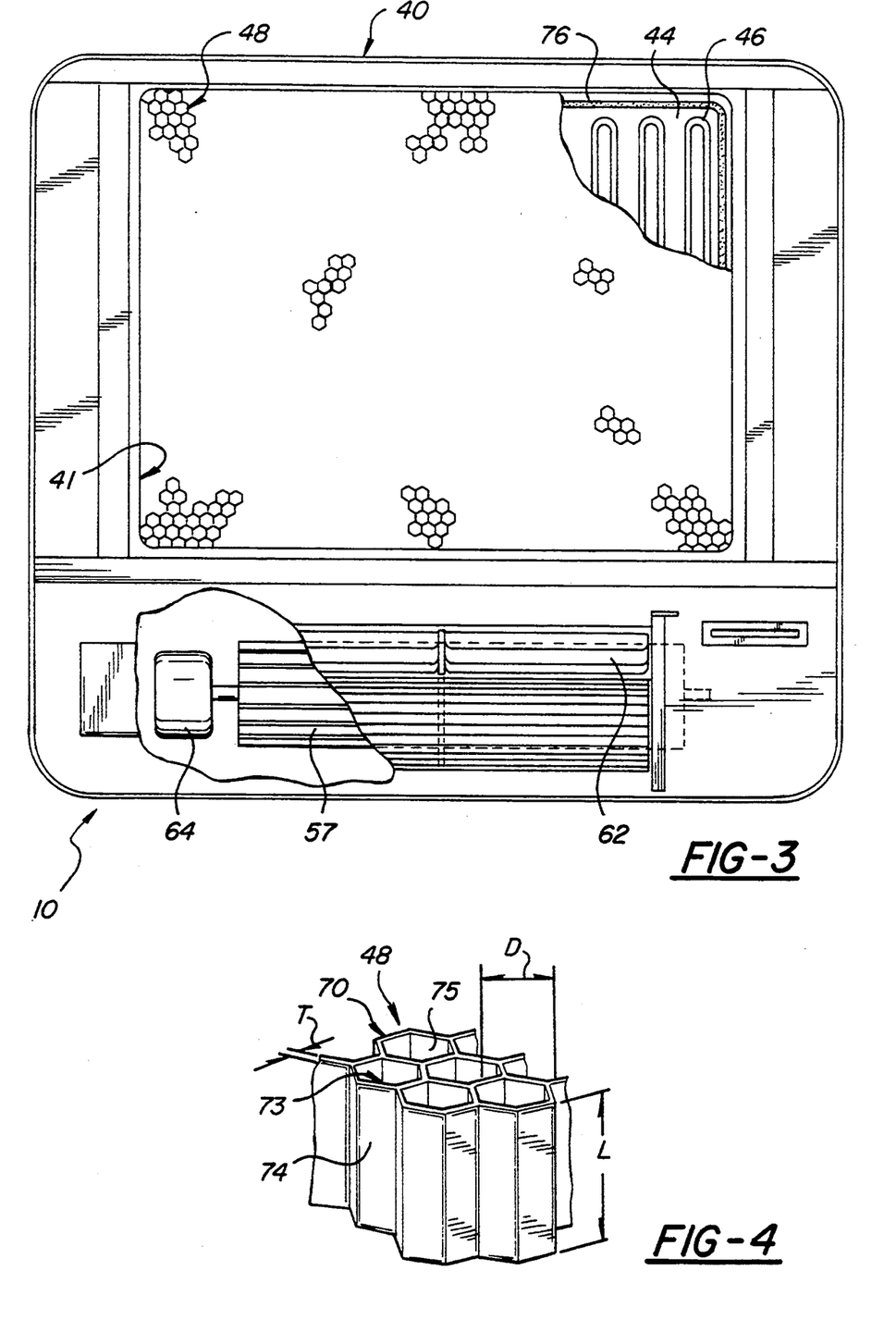
FIG. 3 is a front elevational view of the heating apparatus partially broken away.
FIG. 4 is a fragmentary perspective view of a portion of the stagnating means of the invention.

The heating apparatus 10 additionally comprises stagnating means comprising an air stagnating element 48 also disposed in the housing, comprising a plurality of conduits or tubes 70 in a coherent array defining a first zone 77 which includes a pocket 73, as shown in greater detail in FIG. 4. The tubes or conduits 70 have first 71 and second 72 open ends and a wall portion 74 extending therebetween. The tubes 70 may be of any desired cross-section, although a hexagonal cross-section is the preferred form. The stagnating element 48 is held in place against the radiation generating element 42 by compression. An insulation pad 50 formed of ceramic fibers and having a stainless steel specular reflector plate 52 affixed thereto is disposed in the housing 40 in spaced-apart relationship behind the surface of the radiation generating element 42. A thermo-sensing probe 54 is positioned in the base block 44, and is connected to an electrical temperature control unit 56 of the type well known in the art. An air circulating means for circulating air over the object being irradiated is mounted within the housing 40. The air circulating means comprises a fan housing 58 having a motor cooling fan 60 mounted therein, and a cylindrical fan 57, shown in greater detail in FIG. 3, the air therefrom passing via duct 59 through an adjustable louvre assembly 62.

Referring to FIGS. 3 and 4, the infrared heating apparatus 10 of the invention is shown in a front elevational view. The air stagnating element 48 formed of the plurality of tubes 70, and the adjustable louvre assembly 62 are shown in greater detail.

Figures 5, 6:
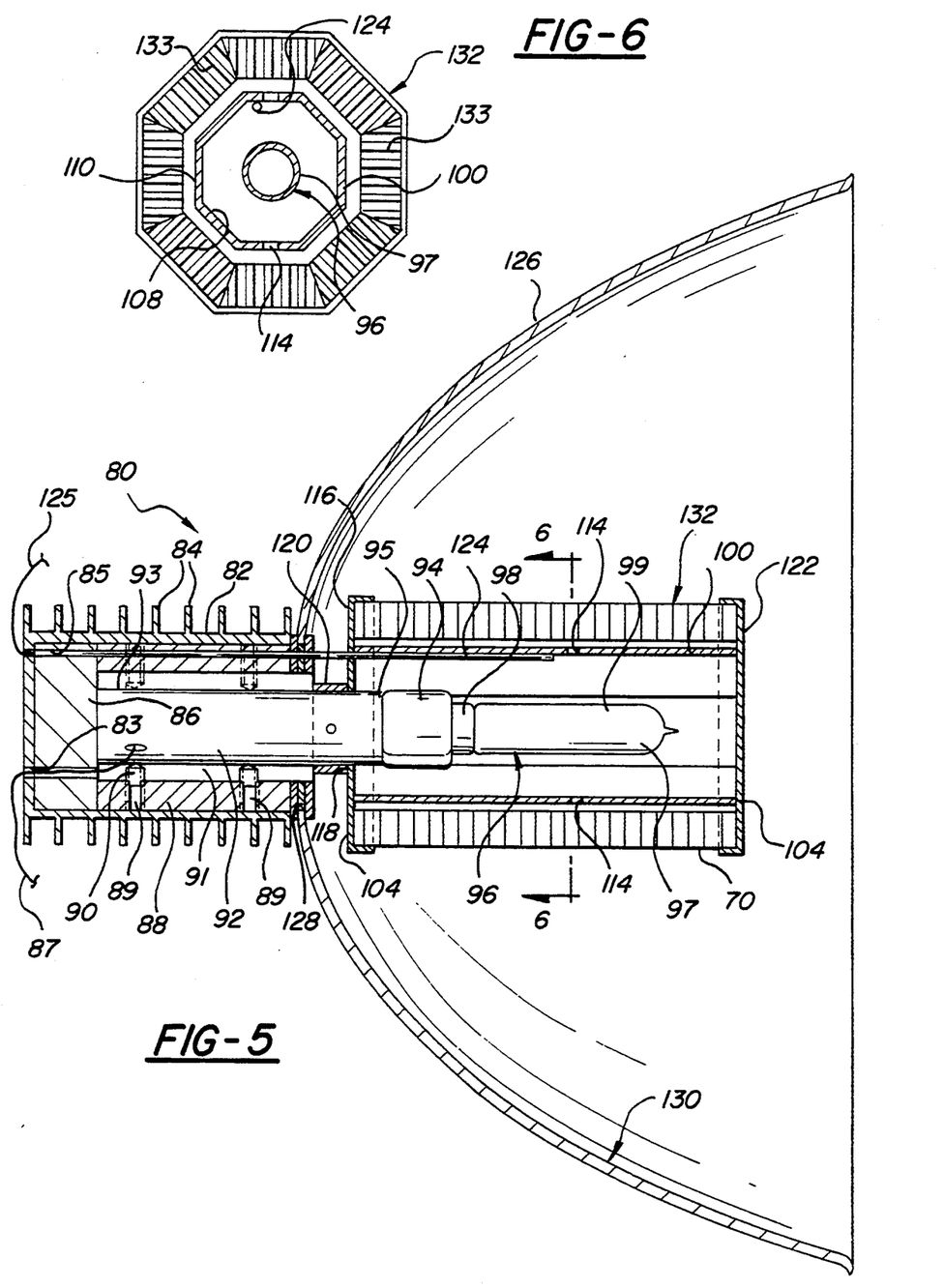
FIG. 5 is a cross-sectional view of another embodiment of the heating apparatus of the present invention.
FIG. 6 is a cross-sectional view taken substantially along line 6—6 of FIG. 5.

Referring to FIGS. 5 and 6, another embodiment of the infrared heating apparatus 10 is shown and indicated by the reference numeral 80. The apparatus 80 of the second embodiment comprises a housing 82 having a plurality of cooling fins 84. Within the housing 82 is a base insulating plug 86 of a material such as ceramic fiber, a sleeve 88, and a plurality of apertures 89 with set screws 90 located therein. Adjustably supported on the set screws 90 is a slidable cylinder 92 creating an air space 91 between the slidable cylinder 92 and the sleeve 88. An aperture 83 is provided in the housing 82 so that a power cord 87 can be connected to a lamp socket 94 disposed in the slidable cylinder 92. The lamp socket 94 is mounted on an end 95 of the cylinder 92. A radiation source 96 comprising a lamp 97 having a base section 98 and radiation-emitting section 99 is mounted in the socket 94. A tubular element 100, mounted around the lamp 96, is formed of a metal having apertures 114 provided therein, and serves to absorb visible light and to emit infrared light therefrom and will be subsequently described in detail.

A stagnating means comprises a tubular air stagnating element 132 mounted around the lamp 96 and the tubular element 100 between a rear cap 116 and a front cap 122. The rear cap 116 has a central aperture 118 provided therein and an axial flange 120 affixed to the slidable cylinder 92 by welding or any other suitable means. The air stagnating element 132 is formed as an octagonal tube comprised of eight individual sections 133. A thermo-sensing probe 124 is positioned in contact with the tubular element 100, and is connected to a remote electrical temperature control unit, not shown. A wire 125 connected to the thermo-sensing probe 124 exits the housing 82 and the insulating block 86 through an aperture 85 and is connected to the remote electrical temperature control unit, not shown, to be subsequently described in detail. A reflector 126 having a central aperture 128 is mounted to the housing 82 for directing the infrared light emitted from radiation generating element 96 in a narrow beam or focusing the radiation into a spot. The reflector 126 may have a parabolic, hyperbolic, elliptical, or any other suitable form depending on the application for which the apparatus is used.

Figure 7:
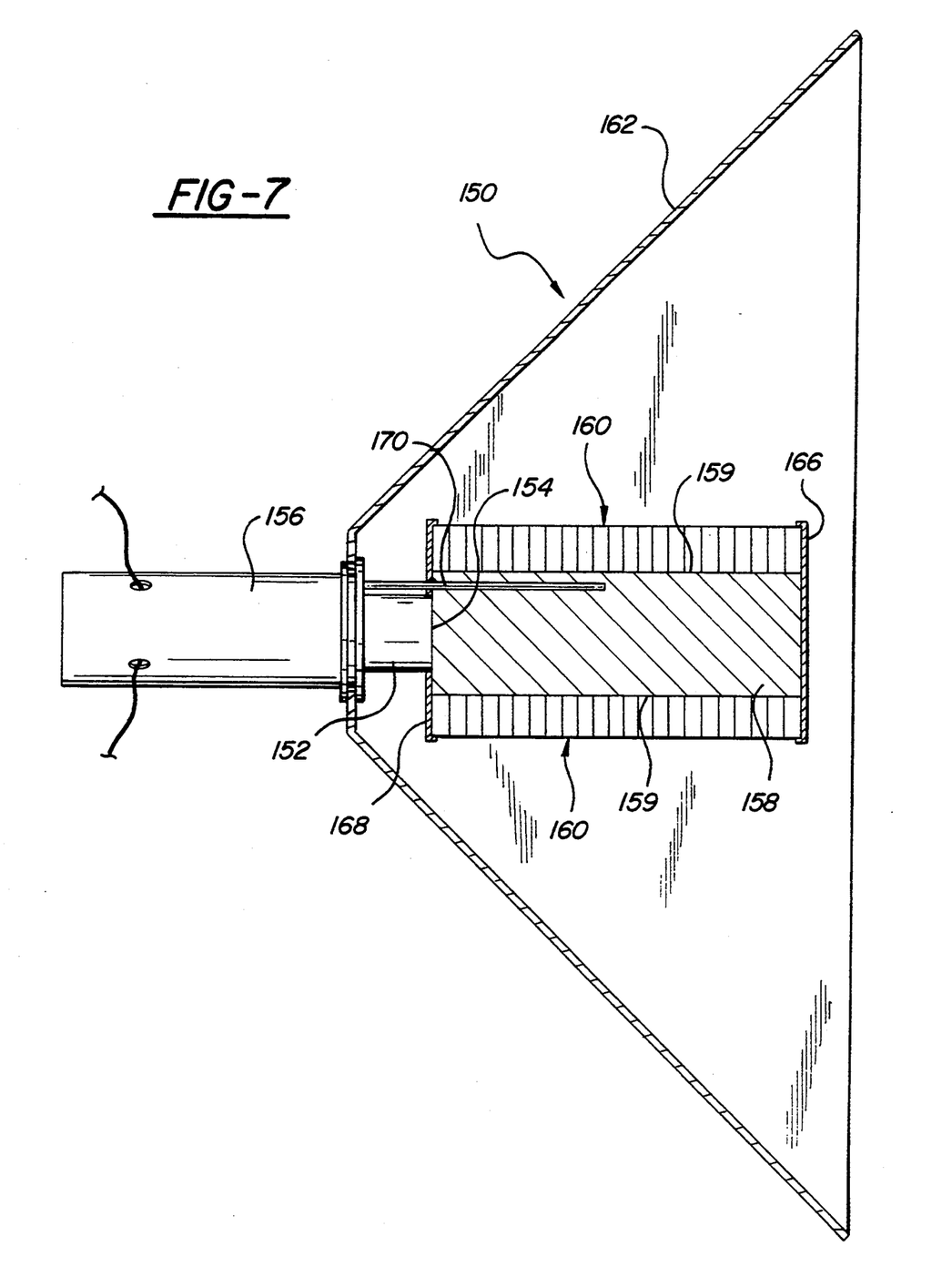
FIG. 7 is a cross-sectional view of still another embodiment of the heating apparatus of the present invention.

Referring to FIG. 7, a third embodiment of the infrared heating apparatus 10 of the present invention is indicated by the reference numeral 150. The apparatus 150 comprises an elongate support 152 and a radiation source comprising a planar radiation generating element 158 similar to that designated by the numeral 42 in FIG. 2. The planar radiation generating element 158 is affixed to a pair of air stagnating elements 160 similar to that designated by the numeral 48 of FIG. 2. The stagnating elements 160 are mounted one on each surface 159 of the radiation generating element 158 and are held in place with front cap 166 and rear cap 168. The support 152 has a first 154 and second 156 ends. The radiation generating element 158 is affixed to the first end 154 of the elongate support 152. The rear cap 166 may be affixed to the first end 154 of the elongate support 152 by welding, crimping, or any other suitable means known in the art. A reflector 162 having a "V" shaped cross-section is mounted to the elongate support 152.

Electrical control means, not shown, but similar to that used with respect to the embodiment shown in FIGS. 5 and 6 are utilized in conjunction with a thermosensing probe 170, which is embedded in the radiation generating element 158.

The terms black body and black body radiation used to describe the radiation source and the radiation emitted from the source but are more accurately termed as a grey body or grey body radiation. At a given temperature, the grey body has the same spectral characteristics as a true black body but at a lower emissivity. Therefore, any reference within to a black body or black body radiation should be understood to mean a grey body or grey body radiation.

The black body infrared radiation generating apparatus comprises a radiation generating element 42 and a stagnating element 48. The radiation generating element 42 is a black or grey body thermal source and, therefore, the radiation source behaves according to the Stefan-Boltzman law.

$$E = nT^4$$

where: $E$ = total energy per area $(W/m^2)$;

$n = 5.67 \times ^{-8} W/(m^2 K^4)$;

T = operating temperature in °K.

Under the Stefan-Boltzman law, the maximum wavelength is a function of the absolute temperature of the black or grey body radiation source. The maximum wavelength is the wavelength at which the maximum power per unit area is generated for a given operating temperature.

$$\text{Maximum Wavelength} = c/(\text{const.} \times T)$$

where: $c = 3.00 \times 10^8 m/s$;

const. $= 5.88 \times 10^{10}$ Hz/°K.

T = operating temperature in °K.

Following the Stefan-Boltzman law, the temperature of the radiation generating element 42 in the apparatus 10 is maintained in a range of about 500°-1000° K. Maintaining the temperature of the radiation generating element 42 in this temperature range yields a black body infrared radiation emission spectrum with maximum emitted wavelengths ($\lambda_{max}$) of approximately 3-6 μm. The maximum emitted wavelengths ($\lambda_{max}$) are the peak emissions, however, radiation emitted from a black or grey body radiation source is emitted in a somewhat continuous spectrum. Therefore, by the nature and physics of a black or grey body radiation source, a range of wavelengths are emitted, not a monochromatic or single wavelength of radiation. The actual continuum emission spectrum for a black or grey body source with maximum emitted wavelengths ($\lambda_{max}$) of approximately 3-6 μm would be approximately 1-30 μm. Additionally, since E, the total energy per area, varies as a function of the temperature to the fourth power ($T^4$), maintaining the temperature of the source is critical to achieving maximum efficacy of the radiation source. In other words, fluctuations in the temperature of the radiation source are reflected exponentially in the total energy per area or power output of the radiation source. For this reason, maintaining the temperature of the radiation source is critical to maximizing efficacy in a given application.

In the preferred embodiment, the radiation generating element 42 is an electrical planar radiant heater. The radiation generating element 42 has at least one flat emitting surface 43 for emitting radiation. The radiation emitted from the planar radiation generating element 42 is uniformly emitted from the emitting surface 43, that is, at any given point above the emitting surface 43, the radiation power density ($W/m^2$) is uniform. The radiation generating element 42 comprises a sinuated heating element 46 embedded therein. The radiation generating element 42 is made of a highly emissive material which is preferably ceramic, similar to the Watlow Raymax ™ ceramic fiber radiant heater. The radiation generating element 42 can also be made from copper, aluminum, or any other suitable material capable of operating in the 500°-1000° K. temperature range and may be chemically blackened or etched as known in the art.

The operating temperature of the radiation generating element 42 is controlled by a temperature control means 54,56. The temperature control means 54 may include a closed loop temperature control using a thermocouple or other thermostatic means. In the alternative, control of the operating temperature of the radiation generating element 42 can be dissipation limited, that is, the operating temperature of the radiation generating element 42 can be controlled by introducing a quantity of energy into the radiation generating element 42 calculated to achieve a particular operating temperature, limited by dissipation.

In the preferred embodiment of the apparatus, a thermocouple control unit 56 having a probe or thermal sensor 54 embedded within the base block 44 of the radiation generating element 42 relays temperature information to the thermocouple control unit 56 via wire 55. The control unit 56, located within the housing 40, controls the temperature of the radiation generating element 42 by varying the amount of energy introduced into the radiation generating element 42 thereby adjusting maintaining the temperature of the radiation generating element 42 at a desired temperature.

According to the present invention, the stagnating means comprises a stagnating element 48 for stagnating flow of a fluid medium, such as air, adjacent the radiation generating element 42. A first zone 77 is located adjacent the radiation generating element 42 and extends to a point where it meets a second zone 78. The first 77 and second 78 zones include at least one pocket 73. The second zone 78 is located between the first zone 77 and the subject or object 34 being irradiated. The second zone 78 may begin where the first zone 77 ends, that is, the second zone 78 begins at a point within the conduits 70 where the first zone 77 ends. In other words, the first zone 77 and the second zone 78 may intersect each other at a spaced apart distance from the second ends 72 of the conduits 70. The fluid medium extends from the radiation generating element 42 into the first zone 77 and thereafter into the second zone 78. The fluid medium is homogenous, that is, the fluid medium consists of a single constituent such as air, a liquid, a gas, or a vacuum which is evenly and consistently distributed throughout the first 77 and second 78 zones. The fluids comprising the medium can be pure liquids or gases or can be mixtures of liquids or gases. The fluid medium must also be continuous, that is, there can be no breaks or gaps in the medium as it extends into and through the first 77 and second 78 zones. For example, in the preferred embodiment, the fluid medium is air. The air extends from the radiation generating element through the first zone 77 to the second zone 78 without any interruption. In other words, there are no impediments or barriers disposed within the medium which can divide or dissect the fluid medium into discrete and/or disjunct regions.

The fluid medium extends from the radiation generating element 42 through the pocket 73 and through the first 77 and second 78 zones. The stagnating element 48 is comprised of at least one pocket 73, a sub-zone of the first 77 and second 78 zones, located within a conduit or tube 70 having first 71 and second 72 open ends, and a wall portion 74 extending therebetween. The pockets 73 are only a sub-zone or subset of the entire first 77 and second 78 zones.

In the preferred embodiment, the stagnating element 48 comprises a plurality of these pockets 73 with each of the pockets being hexagonally shaped. The hexagonally shaped pockets 73 are arranged in a honeycomb or grille-like structure. The honeycomb structure allows for a greater number of pockets 73 to be utilized for stagnating a fluid medium, such as air, in the first zone 77 located adjacent the radiation generating element 42.

The conduits 70 defining the pockets 73 are conventionally fabricated from a material having low thermal conductivity such as stainless steel, a ceramic material, glass or the like. The inner surfaces 75 of the wall portion 74 of each of the conduits 70 are highly reflective at infrared wavelengths, that is, black body infrared radiation emitted by the radiation generating element 42 is not absorbed by the inner surfaces 75 of the conduits 70, but, rather, the inner surfaces 75 reflect the infrared radiation in a direction away from the radiation generating element 42. The inner surface can comprise coating or plating with such materials as aluminum, nickel, gold, stainless steel, or the like.

Each of the conduits 70 defining the pockets 73 have a length L, a diameter D, and a wall thickness T. In the preferred embodiment, the cross-sectional area of the wall thickness T of each of the wall portions 74 of the conduits 70 is less than the cross-sectional areas of each of the pockets 73 defined by the wall portions 74. In other words, when a cross-section of a conduit 70 defining each of the pockets 73 is analyzed, the area occupied by the wall thickness T should be less than the area of the pocket 73 defined by the wall portion 74. By maintaining a greater ratio of pocket area to wall thickness area, conductive heat loss is minimized and increases power transfer efficiency of the radiation generating element 42. In addition, in the preferred embodiment, the length L of each of the conduits 70 is substantially greater than the diameter D of the pockets 73 defined by the wall portions 74. In other words, each conduit 70 should have a length L which is several times greater than the diameter D of the pockets 73 as defined by the wall portions 74. Ideally, the aspect ratio of conduit or tube 70 length (L) to diameter (D) should be approximately 5-6:1. This relationship more effectively prevents the flow of air from travelling down the pockets 73 defined by the conduits 74 to the radiation generating element 42 and, thus, better inhibits convective heat loss from the radiation generating element 42. The stagnating element 48 prevents convective heat transmission by utilizing the inherent viscosity of the medium, i.e., air, to prevent the flow of the medium. By maintaining aspect ratio of conduit or tube 70 length (L) to diameter (D) in the range of approximately 5-6:1, the viscosity of air substantially prevents the sustenance of convective air currents. In other words, air is not able to freely flow within the conduits or tubes 70.

A sealing means is disposed between the radiation generating element 42 and the first open end 71 of each of the conduits 70 making up the stagnating element 48 to form a substantially air-tight seal between each of the conduits 70 and the radiation generating element 42. The sealing means inhibits convective heat loss from the radiation generating element 42 by preventing circulation of air at or near the radiation generating element 42. In other words, creating the seal between each of the conduits 70 and the radiation generating element 42 prevents air from circulating between the radiation generating element 42 and the first open end 71 of each of the conduits 70 and, thereby, limiting the convective removal of heat from the radiation generating element 42 by the air. Limiting convective heat loss increases the power transfer efficiency of the radiation generating element 42. The sealing means may be any suitable means for creating a seal such as a placing the stagnating element 48 in close proximity to the radiation generating element 42 to create an interface between the stagnating element 48 and the radiation generating element 42 which prevents air flow at the interface. Alternatively, the sealing means may comprise a gasket 76 placed between the radiation generating element 42 and the stagnating element 48 may be used to create the seal between the conduits 70 comprising the stagnating element 48 and the radiation generating element 42. The gasket 76 may be located about a periphery of the radiation generating element 42 for sealing and separating the conduits 70 from the radiation generating element 42. The gasket 76 may be made from material capable of withstanding sustained temperatures in excess of the operating temperatures of the radiation generating element 42. The preferred material being a ceramic material such as ceramic paper. Any suitable means, as is known in the art, for creating a seal may be employed.

The stagnating element 48 and the radiation generating element 42 are held in place within the housing 40 by compression. The specular reflector plate 52 reflects radiation emitted from side opposite the emitting surface 43 away from the interior of the housing 40. The layer of ceramic fiber insulation 50 insulates the interior of the housing 40 from intense heat generated by the radiation generating element 42. The layer of insulation 50 is spaced apart from the radiation generating element 42 but may be located in contact with the radiation generating element 42. The open face 41 of the housing 40 allows for emission of the black body infrared radiation from the radiation generating element 42. The housing 40 also houses air circulating means which comprises a fan 60 for cooling an electric motor 61 contained in the fan housing 58 and the cylindrical fan 57 to the force flow of air through a duct portion 59 of the fan housing 58 to cool external tissues during irradiation. Fan forced air exits the housing 40 through the adjustable louver assembly 62. The adjustable louver assembly 62 allows the flow of air to be directed over the external tissues.

In the first alternative embodiment of the present invention shown in FIGS. 5 and 6, the black body infrared radiation generating apparatus 80 is comprised of a radiation source 96, focusing means for focusing radiation emitted by the radiation source 96, and stagnating means for stagnating air adjacent the radiation source.

The radiation generating apparatus 80 is a focused source, that is, the infrared radiation emitted is concentrated per unit area. In other words, at any given point adjacent the radiation source 96, the radiation power density (W/m$^2$) is not uniform. The radiation source 96 in the first alternative embodiment is a light bulb 97. The light bulb 96 may be of any suitable type or size which is capable of emitting radiant energy. A quartz halogen light bulb is preferable. The light bulb 97 has a base portion 98 and a light emitting portion 99. The base portion 98 of the bulb 97 is removably secured in an electrical socket 94 as is commonly used in the art. This alternative embodiment 80 also includes means for controlling the temperature of the radiation source 96. As shown in FIG. 5, a thermo-sensing probe 124 is located in contact with the tubular element 100 for relaying temperature information to the remote electrical temperature control unit (not shown) similar to the unit 54 previously described. Additionally, the temperature of the source 96 may be dissipation limited as was previously described.

The focusing means comprises a reflector 126 for focusing the radiation emitted by the radiation source 96 on the biological tissue, the tubular element 100 which encloses the radiation source 96, and adjustment means for adjusting the focus of the radiation emitted by the radiation source 96.

The reflector 126 is used to adjustably focus the radiation emitted from the radiation source 96 on a limited portion of the biological tissue. The reflector 126 is oriented about the radiation source 96, with the radiation source 96 axially located. The shape of the reflector 126 is essentially ellipsoidal. However, the shape of the reflector 126 is not limited to that of an ellipse. The shape of the reflector 126 may be parabolic, hyperbolic or any other shape depending on the application, that is, depending on the area of the tissue to be treated, the shape of the reflector 126 is chosen to give a radiation pattern commensurate with the area of tissue to be irradiated. The reflector 126 has an internal reflecting surface 130. The reflecting surface 130 should have specular or mirror-like properties. In order to obtain a reflector 126 having specular properties, the reflector 126 should be constructed of a material or having a coating that is reflective to infrared wavelengths, such as aluminum, silver, nickel, chromium, or gold. In order to limit the material cost, the reflector 126 can be constructed of less expensive materials such as plastic; subsequently the reflecting surface 130 can be plated or coated with better infrared reflecting materials.

The tubular element 100 includes first 102 and second 104 open ends and a wall portion 106 extending therebetween. The tubular element 100 is octagonally shaped and substantially encloses the radiation source 6. The shape of the tubular element 100 may be any shape capable of enclosing the radiation source 96, however, the shape must be such that a substantially air-tight seal can be formed between the tubular element 100 and the stagnating element 132. The tubular element 100 is constructed of aluminum but, can also be constructed of copper or other suitable thermally conducting materials. The tubular element 100 includes inner 108 and outer surfaces 110. The outer surface 110 of the tubular element 100 is etched and blackened to increase its emissivity. The etching may be done chemically or mechanically and the blackening may be accomplished by chemical means, however both the etching and blackening of the tubular element 100 may be accomplished by any means known in the art. The radiation source 96 is axially located within the tubular element 100.

The tubular element 100 also includes a plurality of spaced apart apertures 114 provided therein permitting a controlled amount of visible light from the radiation source 96 to escape from the tubular element 100. The visible light from the radiation source 96 exits the tubular element 100 through the apertures 114, travels through the stagnating element, and strikes the reflector 126 and is focused and becomes visible to an observer. Because infrared radiation is not in the range of light visible to a human eye, this controlled amount of visible light from the radiation source 96 is used to obtain an approximation of both the size and the focal point of the infrared radiation emitted from the radiation source 96.

The means for adjusting the focus of the radiation is comprised of the slidable cylinder 92 and sleeve 88. The slidable cylinder 92 has first end 93 and second end 95 and is constructed of a thermoconducting material preferably stainless steel. The first end 93 of the slidable cylinder 92 slidingly passes through the aperture 128 in the reflector 126 and is supported by the sleeve 88. The sleeve 88 may be constructed of a low thermally conductive material such as aluminum, and has a plurality of threaded apertures 89 for receiving set screws or fasteners 90 for adjustably securing the slidable cylinder 92 once a desired size and focal point of the emitted radiation is established. The second end 95 of the slidable cylinder 92 is attached to the socket 94 containing the radiation source 96. The adjustment means provides a mechanism by which the radiation source 96 can be moved relative to the reflector 126 for focusing the radiation emitted from the radiation source 96.

In order to adjust the focus of the radiation generating apparatus 80, the operator first loosens the set screws 90 of the sleeve 88, manually adjusting the position of the radiation generating element 96 by sliding toward or away from the reflector 126 until the desired focal point is obtained, and then re-tightening the set screws. FIG. 3 shows the radiation generating source 96 in its fully retracted position. Additionally, the focus of the apparatus 80 may be accomplished by utilizing the well known focusing helix as is commonly employed in adjustable lenses such as camera lenses.

The cylindrically shaped housing 82 encloses the sleeve 88 and abuts the reflector 126. The cylindrically shaped housing 82 contacts the sleeve 88 to allow for conductive heat transfer from the sleeve 88 to the housing 82. The housing 82 includes a plurality of spaced-apart cooling fins 84 located circumferentially about the housing 82 for dissipating heat generated by the radiation source 96 and transferred through the sliding cylinder 92 to the sleeve 88. The housing 82 is constructed of a thermally conducting material, preferably aluminum. The housing 82 may be secured by known fastening means.

In the embodiment shown in FIG. 6, the stagnating element 132 for stagnating air adjacent the radiation source 96 utilizes the honeycomb structure as previously described, however, the stagnating element 132 surrounds the tubular element 100 containing the radiation source 96. The stagnating element 132 is comprised of eight individual sections 133 of honeycomb material arranged in an octagonal configuration. However, the arrangement of the honeycomb material is not limited to the octagonal configuration and can include any geometric arrangement capable of surrounding the radiation source 96. The individual sections are joined by suitable means such as welding to form a hollow structure capable of surrounding the radiation source 96.

The front cap 122 and the rear cap 116 cover a first 134 end and a second 136 end, respectively, of the stagnating element 10. The front cap 122 and the rear 116 cap each have a shape that is identical to the configuration of the individual sections 133 comprising the stagnating element 132. For example, if the sections of honeycomb material are arranged in an octagonal configuration, the front cap will have an octagonal shape. The front cap 122 and the rear cap 116 are placed in force fitting frictional contact with the respective ends of the conduits of the stagnating element 132. The rear cap 116 includes an aperture 118 for receiving the slidable cylinder 92. The axial flange 120 of the rear cap 116 surrounds the slidable cylinder 92 and is affixed to the slidable cylinder 92 by welding or other suitable means.

In second alternative embodiment of the present invention shown in FIG. 7, the structure of the individual components are the same or similar to those enumerated in the preferred embodiment as described above with the exception of the components listed below. The infrared heating apparatus 150 comprises the planar radiation generating element 158, the pair of air stagnating elements 160, the reflector 162, and elongate support 152 connected to a support stand, not shown. The radiation generating element 158 is similar to that designated by the numeral 42 in FIG. 2 and is attached to a first end 154 of the elongate support 152. However, in this alternative embodiment, both emitting surfaces 159 of the radiation generating element 158 are utilized as radiation emitting surfaces 159. By utilizing two radiation emitting surfaces 159, the radiation emitting surface area is increased and the efficiency of the radiation generating apparatus is thereby increased. Each of the individual stagnating elements 160 of the second alternative embodiment is similar to that designated by the numeral 48 of FIG. 2 and are mounted one on each emitting surface 159 of the radiation generating element 158.

The reflector 162 is affixed to the elongate support 152. The elongate support 152 is made from a material having low thermal conductivity such as a temperature resistant plastic. A remote electrical temperature control means, not shown, similar to that used with respect to the embodiment shown in FIGS. 5 and 6 is utilized in conjunction with the radiation generating element 158 to regulate the temperature of the radiation generating element 158. The reflector 162 is oriented about the radiation generating element 158, with the radiation generating element 158 axially located. The reflector 162 is essentially "V" shaped. However, the shape of the reflector 162 is not limited to being "V" shaped. The shape of the reflector 162 can be any other shape depending on the application, that is, depending on the area of the tissue to be treated, the shape of the reflector 162 is chosen to give a radiation pattern commensurate with the area of tissue to be irradiated.

In operation, the portion of the body 34 to be treated, disposed in the second zone 78, is placed in the fluid medium in spaced apart relationship to the infrared heating apparatus 10,80,150. An electrical current, not shown, is applied to the radiation generating element 42,96,158. The temperature of the radiation generating element 42,96,158 is maintained in the range of about 500°–1000° K. by the thermocouple temperature control unit 56 which varies the amount of electrical current supplied to the radiation generating element 42,96,158, thereby controlling the temperature of the radiation generating element 42,96,158. Controlling the temperature of the radiation generating element 42,96,158 in about this temperature range causes the radiation generating element 42,96,158 to emit black or grey body infrared radiation with maximum emitted wavelengths ($\lambda_{max}$) of approximately 3–6μ, yielding an emission spectrum in the range of about 1–30 μm. The stagnating element 48,132,160 inhibits the flow of the fluid medium, such as air, in the first zone 77 located adjacent the radiation generating element 42,96,158 thereby reducing convective heat loss from the radiation generating element 42,96,158 and also inhibiting the heating of the air in the second zone 78 which is located adjacent the first zone 77 and spaced apart from the second end 72 of the conduits or tubes 70. This is achieved by each of the conduits or tubes 70 defining the first 77 and second 78 zones which include pockets 73 for stagnating or trapping air therein. In addition to reducing convective heat loss from the radiation generating element 42,96,158, the conduits or tubes 70 inhibit the flow of air by producing the pocket 73 containing stagnant air. This pocket 73 of stagnant air provides an insulative layer of air between the radiation generating element 42,96,158 and the external tissues of the portion of the body 34 being heated located in the second zone 78. This insulative layer of air reduces the heating of the external tissue by preventing the heating of air between the radiation generating element 42,96,158 and the external tissues, thereby, increasing the maximum exposure time allowing for a longer and more beneficial treatment. In other words, a pocket or zone 73 of stationary air is maintained allowing for the transmission of radiant energy in the form of infrared radiation while inhibiting the passage of thermal energy in the form of convectively heated air thereby allowing the internal tissues to be heated while protecting the external tissues from damage. The effect of the insulative layer of air increases the efficiency of the radiation generating element 42,96,158 by reducing the amount of heat loss from the radiation generating element 42,96,158 to its surroundings. Since the electrical power coming into the radiation generating element 42,96,158 essentially only heats the radiation generation element 42,96,158 and, then, is emitted to heat the subject 34, very little power is wasted heating up the surrounding air. The insulative layer of air trapped by the stagnating element 48,132,160 essentially creates a quasi-vacuum around the radiation generating element 42,96,158 isolating the radiation generating element 42,96,158 from the surrounding air and increasing the power efficiency of the radiation generating apparatus 10,80,150. The black body infrared radiation emitted from the radiation generating element 42,96,158 so that black body infrared radiation from the radiation generating element 42 enters through the first open end 71 and exits through the second open end 72 passing through the pockets 73, the first 77 and second 78 zones of the stagnating element 48,132,160, and through the fluid medium to the second zone 78 where it may then be applied to biological tissues.

The method is disclosed for heating internal biological tissues of the type having external tissues without increasing the temperature of the external tissues above a predetermined limit where discomfort or damage to the external tissues occurs. The external biological tissues are understood to include, but are not to be limited to, human or animal skin and the tissues comprising the skin. The internal biological tissues are understood to include, but are not limited to, the tissues lying below the external tissues including muscle, blood vessels, fat, cartilage, bone, tendon, internal organs and the like. Medical literature indicates that external tissue temperatures above a predetermined limit of 45° C. can cause discomfort or even damage to the external tissues.[1] The method includes the steps of generating black body infrared radiation from a black body infrared radiation emitting source 42,96,158 to cause black body infrared radiation having wavelengths primarily in a range of about 3–30 μm to be emitted by maintaining the temperature of the radiation source 42,96,158 in a range of about 500°–1000° K., transmitting the radiation through the first zone 77 and through the second zone 78 to heat the biological tissues located in the second zone 78, establishing a continuous and homogenous fluid medium from the black body infrared radiation emitting source 42,96,158 into the first zone 77 and into the second 78 zone, placing the biological tissue in the fluid medium spaced apart from the apparatus 10,80,150, typically in a range of about ½–12 inches in spaced apart relationship to the radiation source 42,96,158, and applying the black body infrared radiation to the biological tissue to irradiate the biological tissue for a period of time sufficient to increase the temperature of the internal tissue to a therapeutic level e.g., 2 minutes to 6 hours. The method is characterized by stagnating the flow of the fluid medium in the first zone 77 to transmission of heat by convection from the radiation source 42,96,158 and from the first zone 77 to the second zone 78 to heat the internal tissues while preventing the heating of the external tissues above the predetermined limit of 45° C. The temperature increase of the internal biological tissues should be in a range of about 2°–6° C. in order to achieve the therapeutic benefits of hyperthermia.[2] This temperature range has been found to be critical in eliciting the beneficial effects of hyperthermia. The benefits of increasing the temperature of internal biological tissue include but are not limited to treatment of muscle pain and soreness, increasing localized blood flow[3], a treatment for cancers or adjuvant therapy in combination with other cancer or tumor treatments[4] e.g., in combination with ionizing radiation or chemotherapy, treatment for the dermatologic condition of psoriasis[5], faster healing of wounds[6], and changes in mood state.[7] The method further includes the step of circulating air over the external tissue during the application of the black body infrared radiation to remove any excess heat from the external tissues and provide additional comfort to the subject undergoing this method of treatment.

1. Meyer J. L., Kapp D. S., Normal-tissue Effects of Hyperthermia. Front. Radiat. Ther. Oncol. 1989; 23:162–76
2. Robins H. I., Dennis W. H., Neville A. J., Shecterle L. M., Martin P. A., Grossman J., Davis T. E., Neville S. R., Gillis W. K., and Rusy B. F., A Nontoxic System for 41.8° C. Whole-Body Hyperthermia: Results of a Phase I Study Using a Radiant Heat Device, Cancer Research 1985; 45:3937–3944.
3. Hetzel F. W., Biologic Rationale for Hyperthermia, Radiol. Clin. North Am. 1989 May;27(3):499–508.
4. Dunlop P. R., Howard G. C., Has Hyperthermia a Place in Cancer Treatment? , Clin. Radiol. 1989 Jan.; 40(1):76–82.
5. Westerhof W., Siddiqui A. H., Cormane R. H., and Scholten A., Infrared Hyperthermia and Psoriasis, Arch. Dermatol. Res. 1987; 279(3):209–10.
6. Gogia P. P., Hurt B. S., and Zirn T. T., Wound Management with Whirlpool and Infrared Cold Laser Treatment, Phys. Ther. 1988 Aug.; 68(8):1239–42.
7. Koltyn K. F., Robins H. I., Schmitt C. L., Cohen J. D., and Morgan W. P., Changes in Mood State Following Whole-body Hyperthermia, Int. J. Hyperthermia, 1992; 8(3):305–307.

The general steps of the method previously described may also be used as a method for increasing the localized blood circulation in internal biological tissues having external tissues and internal tissues without increasing the temperature of the external tissues above the predetermined limit where discomfort or damage to the external tissues occurs. This method is characterized by stagnating the flow of the fluid medium in the first zone 77 to transmission of heat by convection from the radiation source 42,96,158 and from the first zone 77 to the second zone 78 to heat the internal tissues while preventing the heating of the external tissues above the predetermined limit to increase circulation by localized vasodilation of capillaries and blood vessels. In response to the increased temperature of the internal tissues, the capillaries and blood vessel in the internal tissues undergo vasodilation, i.e., the diameter of these blood carrying vessels increases in order to allow for increased blood flow. The increased blood flow provides for better cooling of the tissues being irradiated through increased tissue perfusion and, additionally, provides for increased nutrient delivery and waste removal from the internal tissues.[3]

3. Hetzel F. W., Biologic Rationale for Hyperthermia, Radiol. Clin. North Am. 1989 May;27(3):499–508.

The general steps of the method as disclosed may also be used as a method for increasing the localized blood circulation in internal biological tissues of a penis. This method also includes the step of repositioning the penis to irradiate the previously unexposed surface of the penis and is characterized by stagnating the flow of the fluid medium in the first zone 77 to transmission of heat by convection from the radiation source 42,96,158 and from the first zone 77 to the second zone 78 to heat the internal tissues of the penis while preventing the heating of the external tissues of the penis above the predetermined limit to increase circulation by localized vasodilation of capillaries and blood vessels.

The method is also disclosed for heating an object with black body infrared radiation comprising the steps of generating black body infrared radiation from a black body radiation source 42,96,158, transmitting the black body radiation through a first zone 77 and thereafter through a second zone 78 to heat the object located in the second zone 78, establishing a continuous and homogenous fluid medium form the black body radiation source through the first zone 77 and through the second zone 78. The method is characterized by stagnating the flow of the fluid medium in the first zone 77 to limit transmission of heat by convection from the radiation source 42,96,158 and from the first zone 77 to the second zone 78. The method also includes the step of maintaining the temperature of the radiation source 42,96,158 in the range of about 500°–1000° K. The method also includes the step of generating black body infrared radiation having wavelengths primarily in the range of about 3–30 μm.

EXAMPLES

Example 1

Using slaughtered pig thighs, a four channel temperature sensor (a custom linear microprobe thermocouple array) was implanted in the internal tissues of the pig thigh. Four independent digital temperature monitoring displays, with a 0.1 degrees C. resolution, were read and recorded every 2 minutes during the test interval.

An infrared heating apparatus such as that shown in FIGS. 1–4, operating at nominally 475 watts was set up and electrical current supplied and adjusted until the infrared apparatus generated infrared energy in a spectrum in the range of 3–30 μm. Both transverse air flow from the fan and normal impingement air flow were used to cool the external epidermal tissues during treatment. After 40 minutes of exposure from the infrared source, the external skin temperature remained under 45° C. The temperature of the internal tissues at a depth of approximately 30 mm rose nominally by 4° C. during the period of treatment.

Example 2

Data was collected comparing the subject infrared heating apparatus operating at 475 Watts, such as that shown in FIGS. 1–4, and a standard heat lamp (250 Watt General Electric Infrared Heat Lamp). The radiant power output (watts) was normalized by adjusting the current supplied to both the subject infrared heating apparatus and the standard heat lamp was adjusted to give nearly identical radiant power outputs per area of tissue irradiated (W/cm$^2$). As in example 1, slaughtered pig thighs were used, a four channel temperature sensor (a custom linear microprobe thermocouple array) was implanted in the internal tissues of the pig thigh. Four independent digital temperature monitoring displays, with a 0.1 degrees C. resolution, were read and recorded every 2 minutes during the test interval.

Both the subject infrared heating apparatus and the standard heat lamp were operating at nominally 0.92 W/cm$^2$ and 0.95 W/cm$^2$, respectively. For the subject infrared heating apparatus, transverse air flow from the fan was used to cool the external epidermal tissues during treatment. Comparing the data points taken after approximately 15 minutes of exposure, the increase in internal temperature, recorded at approximately 32 mm under the surface of the skin, of both the subject infrared apparatus and the standard heat lamp were approximately 2° C. during the period of treatment. However, for the standard heat lamp, the temperature increase of the external tissues was approximately 36° C. compared to only approximately a 12° C. external tissue temperature increase for the subject infrared heating apparatus for the same period of treatment. It was observed during this experiment that at the point at which the temperature of the external tissue had increased by 36° C., burning and other serious tissue damage had occurred.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A method for heating an object with black body infrared radiation, said method comprising the steps of:
   generating black body infrared radiation from a black body radiation source (42,96,158);
   transmitting the radiation through a first zone (77) and thereafter through a second zone (78) to heat the object (34) located in the second zone (78);
   establishing a continuous and homogenous fluid medium from the black body radiation source (42,96,158) through the first zone (77) and through the second zone (78); and
   characterized by stagnating flow of the fluid medium in the first zone (77) to limit transmission of heat by convection from the radiation source (42,96,158) and from the first zone (77) to the second zone (78).

2. The method of claim 1 including the step of maintaining the temperature of the radiation source (42,96,158) in a range of 500°–1000° K.

3. The method of claim 1 wherein the step of generating black body infrared radiation is further defined as generating wavelengths in a range of 3–30 μm.

4. A method for heating internal biological tissues of the type having external tissues without increasing the temperature of the external tissues above a predetermined limit where discomfort to the external tissues occurs comprising the steps of:
   generating black body infrared radiation in the range of 3–30 μm from a black body radiation source (42,96,158);
   transmitting the radiation through a first zone (77) and thereafter through a second zone (78) to heat the biological tissues located in the second zone (78);
   establishing a continuous and homogenous fluid medium from the black body radiation source (42,96,158) through the first zone (77) and through the second zone (78);
   characterized by stagnating flow of the fluid medium in the first zone (77) to limit transmission of heat by convection from the radiation source (42,96,158) and from the first zone (77) to the second zone (78) to heat the internal tissues while preventing the heating of the external tissues above the predetermined limit.

5. The method of claim 4 further including the step of maintaining the temperature of the radiation source (42,96,158) in a range 500°–1000° K.

6. The method of claim 4 further including the step of limiting the temperature of the external tissues to no more than 45° C.

7. The method of claim 4 further including the step of increasing the temperature of the internal tissues in a range of 2°–6° C.

8. The method of claim 4 further including the step of circulating air over the external tissues during the application of the infrared radiation.

9. A method for increasing localized blood circulation in internal biological tissues of having external tissues and internal tissues without increasing the temperature of the external tissues above a predetermined limit where discomfort to the external tissues occurs comprising the steps of:
   generating black body infrared radiation in the range of 3–30 μm from a black body radiation source (42,96,158);
   transmitting the radiation through a first zone (77) and thereafter through a second zone (78) to heat the biological tissues located in the second zone (78);
   establishing a continuous and homogenous fluid medium from the black body radiation source (42,96,158) through the first zone (77) and through the second zone (78);
   characterized by stagnating flow of the fluid medium in the first zone (77) to limit transmission of heat by convection from the radiation source (42,96,158) and from the first zone (77) to the second zone (78) to heat the internal tissues while preventing the heating of the external tissues above the predetermined limit to increase circulation by localized vasodilation of capillaries and blood vessels.

10. The method of claim 9 further including the step of maintaining the temperature of the radiation source (42,96,158) in a range of 500°–1000° K.

11. The method of claim 9 further including the step of limiting the temperature of the external tissues to less than or equal to 45° C.

12. The method of claim 9 further including the step of increasing the temperature of the internal tissues in a range of 2°–6° C.

13. The method of claim 9 further including the step of circulating air over the external tissues during the application of the infrared radiation.

14. A method for increasing the localized blood circulation in internal biological tissues of a penis having external tissues without increasing the temperature of the external tissues above a predetermined limit where injury to the external tissues occurs comprising the steps of:

generating black body infrared radiation in the range of 3–30 μm from a black body radiation source (42,96,158);

transmitting the radiation through a first zone (77) and thereafter through a second zone (78) to heat the internal tissues of the penis located in the second zone (78);

establishing a continuous and homogenous fluid medium from the black body radiation source (42,96,158) through the first zone (77) and through the second zone (78);

applying the black body infrared radiation to an exposed surface of the penis;

repositioning the penis to irradiate previously unexposed surface of the penis; and characterized by stagnating flow of the fluid medium in the first zone (77) to limit transmission of heat by convection from the radiation source (42,96,158) and from the first zone (77) to the second zone (78) to heat the internal tissues of the penis while preventing the heating of the external tissues of the penis above the predetermined limit to increase circulation by localized vasodilation of capillaries and blood vessels.

15. The method of claim 14 further including the step of maintaining the temperature of the radiation source (42,96,158) in a range of 500°–1000° K.

16. The method of claim 14 further including the step of limiting the temperature of the external tissues of the penis to less than or equal to 45° C.

* * * * *